US00PP10642P

United States Patent [19]

Amorao et al.

[11] Patent Number: Plant 10,642

[45] Date of Patent: Oct. 13, 1998

[54] STRAWBERRY PLANT NAMED 'SAN MIGUEL'

[75] Inventors: Amado Q. Amorao, Camarillo; Thomas M. Sjulin, Aromas, both of Calif.

[73] Assignee: Driscoll Strawberry Associates, Inc., Watsonville, Calif.

[21] Appl. No.: 783,391

[22] Filed: Jan. 13, 1997

[51] Int. Cl.[6] ..... A01H 5/00

[52] U.S. Cl. ..... Plt./49

[58] Field of Search ..... Plt./48, 49

[56] References Cited

U.S. PATENT DOCUMENTS

P.P. 3,981 11/1976 Bringhurst et al. ..... Plt./48

P.P. 4,538 5/1980 Bringhurst et al. ..... Plt./49

P.P. 5,265 7/1984 Voth et al. ..... Plt./48

P.P. 7,614 8/1991 Bringhurst et al. ..... Plt./49

*Primary Examiner*—Howard J. Locker

*Attorney, Agent, or Firm*—Pennie & Edmonds LLP

[57] ABSTRACT

This invention relates to a new and distinct variety of strawberry named 'San Miguel'. The variety is similar in appearance to 'Camarosa'. The variety is characterized from 'Camarosa' by its medium plant vigor, medium green length to width ratio of the terminal leaflet, the inflorescence is positioned above the leaves, conical to almost cylindrical fruit shape, red skin color, and fruit flesh that is red and firm. 'San Miguel' possesses unusually long pedicels.

4 Drawing Sheets

BACKGROUND OF THE INVENTION

The new variety of strawberry was discovered as a seedling in a controlled breeding plot in Ventura County, Calif., U.S.A., on or about Feb. 1992. The new variety originated as a result of a controlled cross between the strawberry plants named 'Seascape' (U.S. Plant Pat. No. 7,614) and the Driscoll Strawberry Associates, Inc. variety 'K6'(unpatented) in an on-going breeding program. The original plant of this invention was asexually reproduced by stolons in a nursery in Shasta County, Calif. Propagules were transplanted to a controlled breeding plot in Ventura County, Calif. where the claimed 'San Miguel' variety was identified and selected for further evaluation. Clones of the new variety were further asexually propagated and extensively tested. This propagation and testing has demonstrated that the combination of traits disclosed herein which characterize the new variety were fixed and retained true to type through successive generations of asexual reproduction.

SUMMARY OF THE INVENTION

The present invention relates to a new and distinct strawberry variety. The varietal denomination of the new variety is 'San Miguel'. The variety is botanically identified as *Fragaria×ananassa*. Among the characteristic which distinguish the new variety from other varieties of which we are aware are a combination of traits which include plant vigor, leaf color, length to width ratio of the terminal leaflet, position of the inflorescence, flower size, length of pedicels, fruit shape, fruit skin color, and fruit flesh color and texture.

COMPARISON TO CLOSEST VARIETIES

The variety which we believe to be closest in geographic adaptation and season of ripening to 'San Miguel' from those known to us is 'Camarosa' (U.S. Plant Pat. No. 8,708). There are several characteristics of the new variety that are different from, or not possessed by 'Camarosa'. For example, the plant vigor of 'San Miguel' is medium, while that of 'Camarosa' is strong to very strong as exhibited by 'San Miguel's' lower frequency of crown branching and smaller plant size than 'Camarosa'. The leaf color of 'San Miguel' is medium green, while that of 'Camarosa' is light to medium green. The length to width ratio of the terminal leaflet of 'San Miguel' is broader than long to as broad as long, while that of 'Camarosa' is longer than broad. The position of the inflorescence relative to the leaves for 'San Miguel' is above, while that of 'Camarosa' is below. The flower size of 'San Miguel' is medium to large, while that of 'Camarosa' is small to medium. The fruit shape of 'San Miguel' ranges from conical to almost cylindrical, while that of 'Camarosa' is cylindrical to wedge shaped. The skin color of 'San Miguel' is red, while that of 'Camarosa' is dark red. The fruit flesh of 'San Miguel' is red, while that of 'Camarosa' is dark red. The fruit flesh of 'San Miguel' is firm, while that of 'Camarosa' is extremely firm. 'San Miguel' possesses unusually long pedicels as illustrated in FIG. 1.

Regarding isozyme analysis, the phosphoglucoisomerase (PGI) isozyme banding pattern for 'San Miguel' is A4 while that for 'Camerosa' is A2. The leucine aminopeptidase (LAP) isozyme banding pattern for 'San Miguel' and 'Camarosa' is B3. The phosphoglucomutase (PGM) isozyme banding pattern for 'San Miguel' is C2 while that for 'Camarosa' is C1. See *J. Amer. Soc. Hort. Sci.* 106:684 (1981).

TABLE 1

Isozyme Analysis for 'San Miguel' and 'Camarosa'

| | Cultivar | |
|---|---|---|
| Locus | 'San Miguel' | 'Camarosa' |
| PGI | A4 | A2 |
| LAP | B3 | B3 |
| PGM | C2 | C1 |

'Camarosa' isozyme data from U.S. Plant Patent # 8,708

BRIEF DESCRIPTION OF THE ILLUSTRATIONS

The accompanying photographs show typical specimens of the new variety, including fruit, foliage and flowers, in color as nearly true as it is reasonably possible to make in color illustrations of these characteristics.

DESCRIPTION OF THE NEW VARIETY

Figure 1:
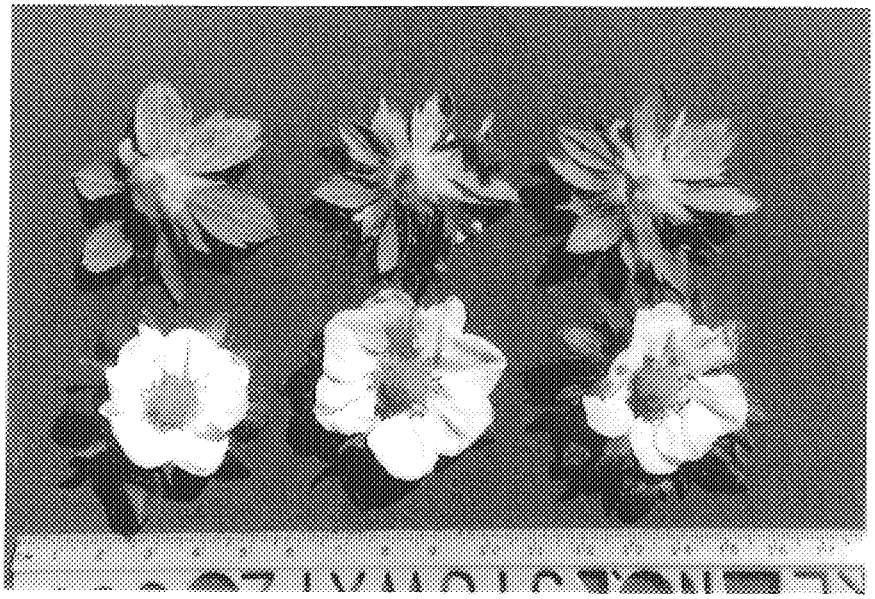
FIG. 1 shows the flower and reproductive organs of the new variety, as well as the size and position of the petals and sepals and the underside of the calyx.
Figure 2:
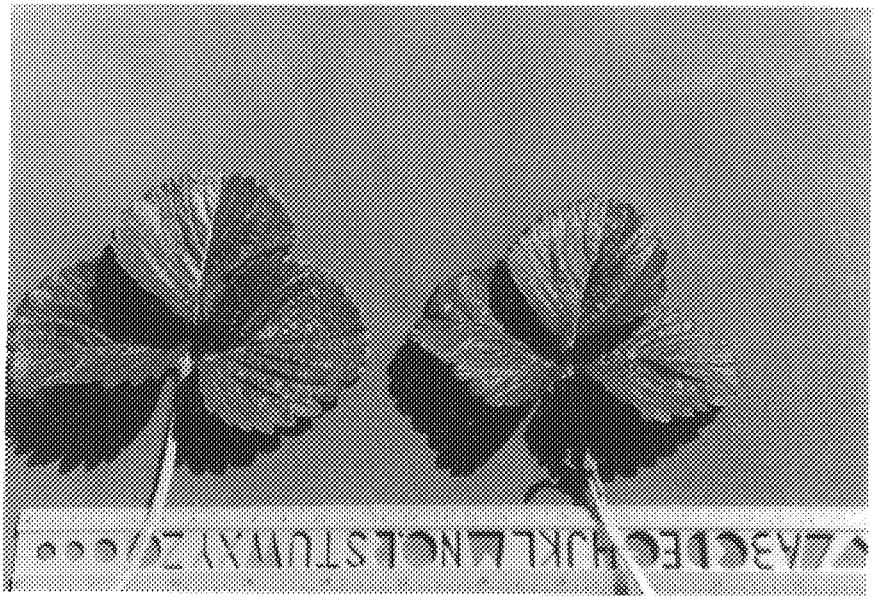
FIG. 2 shows the upper surface of two typical folioles of the new variety.
Figure 3:
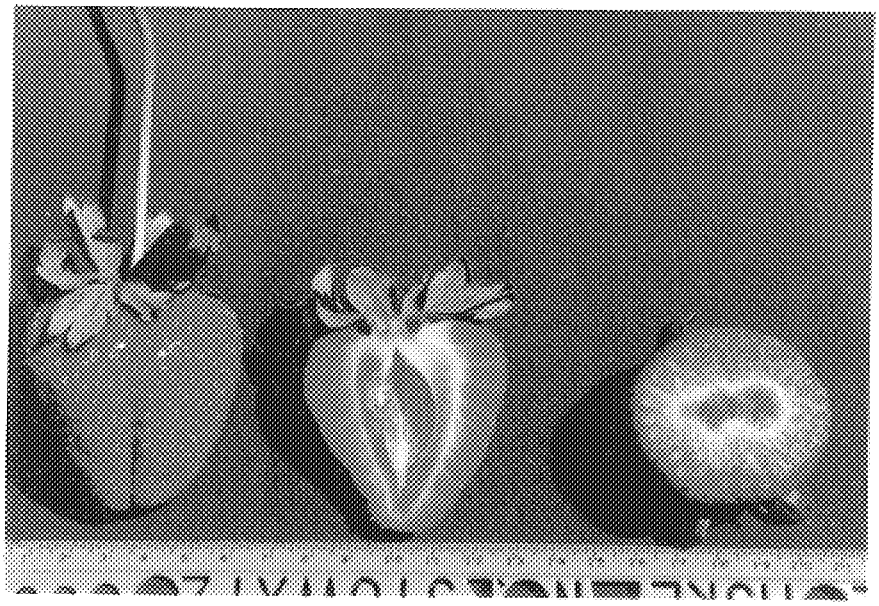
FIG. 3 shows the fruit in longitudinal section and cross section, illustrating the typical flesh and flesh coloration.
Figure 4:
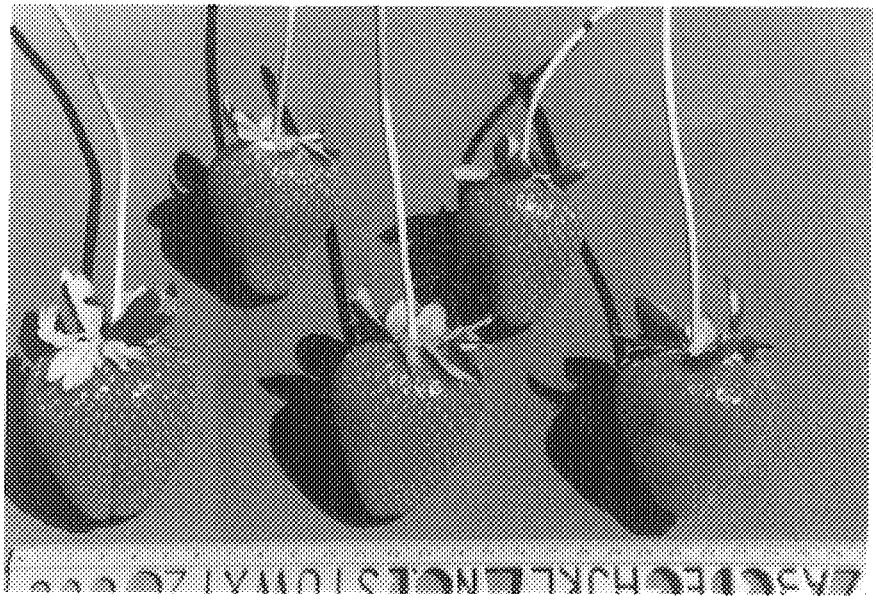
FIG. 4 shows typical whole fruit.

The following detailed description of the new variety is based upon observations taken of plants and fruit grown in experimental test plots in Ventura County, Calif., U.S.A. This description is in accordance with UPOV terminology. Color designations, color descriptions, and other phenotypical descriptions may deviate from the stated values and descriptions depending upon variation in environmental, seasonal, climatic and cultural conditions. Colors are described using standard Munsell Notation.

Propagation

The new variety is principally propagated by way of stolons. Although propagation by stolons is presently preferred, other known methods of propagating strawberry plants may be employed.

Characteristics of the New Variety

The following information is provided to describe the new variety.

Plant:

*Habit.*—Flat globose.

*Density.*—Medium.

*Vigor.*—Medium.

| Average Dimensions - | 'San Miguel' | 'Camarosa' |
|---|---|---|
| Plant height | 16.8 cm | 18.0 cm |
| Plant width | 32.4 cm | 34.3 cm |
| Average number of crowns | 3.8 | 6.9 |
| Day-length response | short day | short day |

(Measurements were taken in Ventura County, California.)

*Chilling requirement.*—'San Miguel' has an optimal chilling requirement of 2 weeks which is slightly higer than that for 'Camarosa' (0–10 days) or 'Chandler' (U.S. Plant Pat. No. 5,262) but lower than 'Seascape' (U.S. Plant Pat. No. 7,614) (4–6 weeks).

*Propensity to form runners.*—'San Miguel' will runner in the fruiting field when given more than 4 weeks of chilling before transplanting. 'San Miguel' has little tendency to form runners without chilling.

Foliage:

Leaf.—Color—upperside—medium green, 0.3G 2.2/4.1. Underside—light gray green; no match of color on Munsell Color Cascade. Profile (angle of leaf where attached to petiole)—flat. Blistering—strong. Number of leaflets—three only.

*Terminal leaflet.*—Profile—revolute to flat. Length to width ratio—broader than long to as long as broad. Shape of base—rounded. Shape of teeth—rounded. Margins—Average number of serrations—'San Miguel' is 21.4; 'Camarosa' is 17.4. 'San Miguel' has an average of 4 more serrations per terminal leaflet.

| | 'San Miguel' | 'Camarosa' |
|---|---|---|
| Average Dimensions - | | |
| terminal leaflet width | 6.0 cm | 5.8 cm |
| terminal leaflet length | 5.9 cm | 6.2 cm |
| Petiole - Pubescence - sparse to medium. Pose of hairs - outwards. | | |
| Average petiole length - | 15.4 cm | 14.6 cm |
| Petiole Color - | 5.3GY 5.2/9.7 | 5.4GY 6.0/11.0 |
| Bracts - | | |
| Average bract length - | 19 mm | NA |
| Bract color - | 2.9GY 2.3/3.6 | NA |

*Frequency of bracts.*—bracts are present on approximately 30% of petioles. Angle of base of bracts—slightly oblique.

*Stolons.*—Number—many. Anthocyanin coloration—weak to medium. Thickness—thin to medium. Pubescence—sparse to medium.

| Stipules - | 'San Miguel' | 'Camarosa' |
|---|---|---|
| Average stipule length - | 32 mm | 28 mm |
| Stipule color - | 5.4GY 6.9/12.6 | 5.6GY 7.6/13.6 |

*Inflorescence.*—Position relative to foliage—above. The height of the inflorescence above the foliage varies during the growing season depending on the plant height, but is consistently above the foliage.

Flower: The flowers described are secondary flowers except where indicated.

*Petal color.*—White; white is not referenced in the Munsell Color Cascade.

*Size.*—Medium to large. Average diameter of primary and secondary flowers for 'San Miguel' is 35 mm and 'Camarosa' is 31 mm. Average diameter of the calyx of 'San Miguel' is 41 mm and 'Camarosa' is 43 mm.

*Diameter of calyx relative to corolla.*—(Primary flowers) larger; (secondary flowers) smaller to same size.

*Diameter of inner calyx relative to outer* (*on secondary flowers*).—Same size.

*Spacing of petals* (*on secondary flowers with* 5 *or* 6 *petals*).—Overlapping.

| | 'San Miguel' | 'Camarosa' |
|---|---|---|
| Petal | | |
| Average length | 16 mm | 12 mm |
| Average width | 17 mm | 12 mm |
| Petal Length/ width ratio | 0.95 | 1.00 |
| Sepal | | |
| Average length | 20 mm | 17 mm |
| Average width | 11 mm | 9 mm |
| Sepal-Length/ width ratio | 1.80 | 1.92 |

Petal length to width ratio (on secondary flowers) - as long as broad.

Fruiting truss - Attitude at first picking - prostrate.

-continued

| | 'San Miguel' | 'Camarosa' |
|---|---|---|
| Length - same as pedicel; long. | | |
| Pedicel - | | |
| Average length | 26.6 mm | 20.3 mm |

Fruit (secondary fruit on one year old plants): All fruit characteristics are similar between primary and secondary fruit, unless specified.

*Ratio of length to maximum width*.—As long as broad.

| | 'San Miquel' | 'Camarosa' |
|---|---|---|
| Primary fruit-Length/width ratio | 1.13 | 1.24 |
| Secondary fruit - Length/width ratio | 1.05 | 1.26 |
| Size - Primary fruit- very large; secondary fruit- large. | | |
| Primary fruit length - | 55 mm | 54 mm |
| Primary fruit width - | 49 mm | 43 mm |
| Secondary fruit length - | 44 mm | 42 mm |
| Secondary fruit width - | 42 mm | 33 mm |

*Predominant shape*.—Conical to almost cylindrical.

*Difference in shapes between primary and secondary fruits*.—Moderate.

*Band without achenes*.—Primary fruit-medium; secondary fruit—narrow to medium.

*Achene coloration*.—Achene coloration varies on strawberry fruit according to how much light the individual achenes are exposed. Achenes exposed to light typically have more anthocyanin pigmentation.

| | 'San Miguel' | 'Camarosa' |
|---|---|---|
| Achene coloration (sunward side) | 8.7R 2.1/6.0 | 6.8R 2.6/9.4 |
| Achene coloration (shade side) | 9.1YR 7.36/15.7 | 1.4Y 7.4/15.2 |

*Unevenness of surface*.—(Primary fruit) medium; (secondary fruit) weak.

*Skin color*.—Red (6.6R 2.9/9.7).

*Evenness of color*.—Even.

*Glossiness*.—Medium to strong.

*Insertion of achenes*.—Below surface.

*Insertion of calyx*.—Set above fruit.

*Pose of the calyx segments*.—Reflexed.

*Size of calyx in relation to fruit diameter*.—(primary fruit) same size to larger; (secondary fruit) smaller to same size.

*Adherence of calyx* (*when ripe for fresh market*).—strong.

*Firmness of flesh* (*when fully ripe*).—Firm. The fruit of 'San Miguel' is firm-melting when bitten as compared to 'Camarosa' which is crunchy when bitten.

*Color of flesh*.—Medium red (6.9R 4.1/16.1).

*Evenness of color of flesh*.—Slightly uneven to even.

*Sweetness*.—Medium to strong.

*Texture when tasted*.—Medium.

*Acidity*.—Medium.

*Time of flowering* (50% at first flower).—Early.

*Harvest maturity* (50% of *plants with ripe fruit*).—Early.

*Type of bearing*.—partially everbearing. Partially everbearing varieties are short-day varieties that will continue to re-flower and fruit under cool conditions, such as those that occur in Coastal California. These varieties stop flowering under warm conditions. A variety is determined to be partially everbearing by observing the flowering characteristics of the plant in cool conditions and looking for vigorous re-flowering.

*Season of Harvest*.—The season of harvest for 'San Miguel' in Ventura County, Calif. typically is approximately from the second week of January to the second week of May. 'San Miguel' starts production approximately 2 to 3 weeks later than 'Camarosa'. *Harvest production*.—In a side by side comparison, the marketable yield for 'San Miguel' was 608 g/plant and 'Camarosa' was 539 g/plant. 'San Miguel' produced 13% more marketable fruit than 'Camarosa'.

Resistance to Stress

The new variety is moderately resistant to high pH and high soil salt levels.

Disease Resistance and Susceptibility

The 'San Miguel' variety is moderately susceptible to *Xanthomonas fragariae*. 'San Miguel' is moderately resistant to Powdery mildew, leaf spots (*Ramularia tulasnei*), leaf blight (*Phomopsis obscurans*), Strawberry mottle virus, and *Zythia fragariae*. 'San Miguel' fruit is moderately susceptible to decay by Botrytis fruit rot.

The 'San Miguel' variety is moderately susceptible to injury by the two-spotted spider mite (*Tetranychus urticae*). 'San Miguel' is susceptible to *Tarsonemus pallidus*, Aphis spp., and lygusbug (*Lygus hesperus*).

What is claimed is:

1. A new and distinct variety of strawberry plant, substantially as shown and described.

* * * * *

UNITED STATES PATENT AND TRADEMARK OFFICE
CERTIFICATE OF CORRECTION

PATENT NO. : PP10,642

DATED : October 13, 1998

INVENTOR(S) : Amorao et al.

It is certified that error appears in the above-identified patent and that said Letters Patent is hereby corrected as shown below:

In the Abstract.

After the words medium green delete the word "length" and add the words --leaf color, broader than long to as broad as long length--

After the words 'San Miguel' and before the word "possesses" on the last line of the Abstract, add the word --also--

Signed and Sealed this

Twenty-sixth Day of September, 2000

*Attest:*

Q. TODD DICKINSON

*Attesting Officer*

*Director of Patents and Trademarks*